United States Patent
Etes et al.

(10) Patent No.: US 6,709,633 B2
(45) Date of Patent: Mar. 23, 2004

(54) DISPOSABLE DEVICES FOR TESTING BODY FLUIDS

(76) Inventors: Donald E. Etes, 4215 Market St., Richfield, IL (US) 60012; Michael H. Sherin, 1111 Broadway, Woodstock, IL (US) 60098

( * ) Notice: Subject to any disclaimer, the term of this patent is extended or adjusted under 35 U.S.C. 154(b) by 115 days.

(21) Appl. No.: 09/302,838

(22) Filed: Apr. 30, 1999

(65) Prior Publication Data

US 2003/0138351 A1 Jul. 24, 2003

(51) Int. Cl.$^7$ .............................................. G01N 33/48
(52) U.S. Cl. ........................ 422/58; 422/61; 436/164; 436/169; 436/808; 436/901
(58) Field of Search ................. 422/56, 58, 61; 436/164, 168, 169, 174, 177, 808, 901

(56) References Cited

U.S. PATENT DOCUMENTS

| | | | | |
|---|---|---|---|---|
| 5,119,830 A | * | 6/1992 | Davis .......................... | 127/771 |
| 5,270,166 A | * | 12/1993 | Parsons et al. ............... | 435/7.4 |
| 5,504,013 A | * | 4/1996 | Senior .......................... | 422/61 |
| 5,916,815 A | * | 6/1999 | Lappe .......................... | 422/58 |
| 5,976,895 A | * | 11/1999 | Cipkowski .................... | 422/58 |

* cited by examiner

*Primary Examiner*—Lyle A. Alexander
(74) *Attorney, Agent, or Firm*—Cook, Alex, McFarron, Manzo, Cummings & Mehler Ltd.

(57) ABSTRACT

A self-contained disposable device to be used in testing a body fluid, particularly urine. The device is in the form of a 3-ply composite comprising an intermediate ply and outer plies on opposite sides thereof. The intermediate ply has a cavity for retaining a test wick and one of the outer plies has a small body fluid inlet opening for body fluid to enter and wet the wick. Preferably an absorbent pad is located opposite the inlet opening. Different segments of the length of the wick are impregnated with a control and selection of test reagents. The device may be circular and serve as a liner for the transparent closure cap of a specimen container or in the form of a paddle to be swished in a specimen of a stream of a specimen. One of the outer plies is transparent at least over the impregnated portion of the test wick.

9 Claims, 2 Drawing Sheets

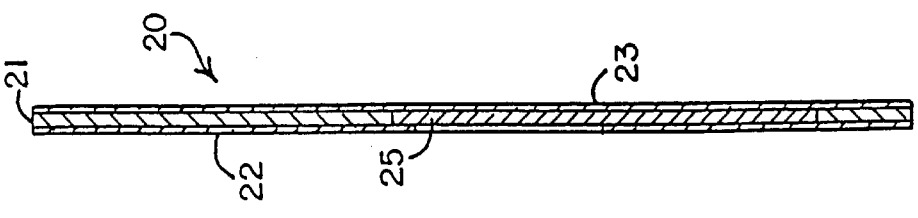
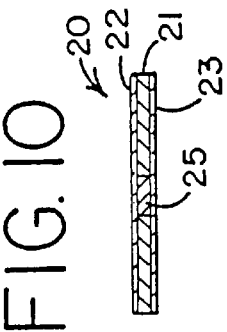
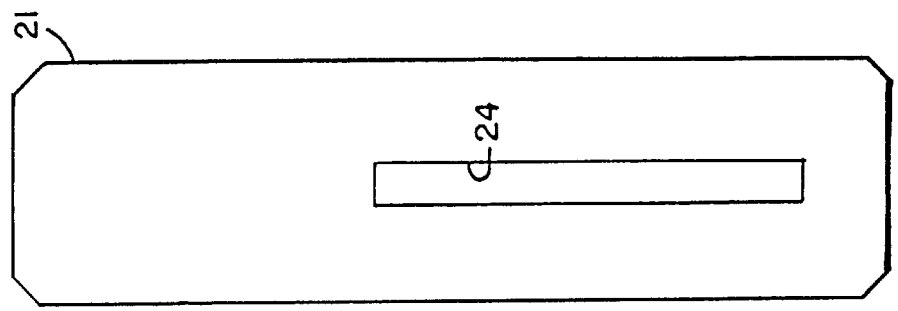
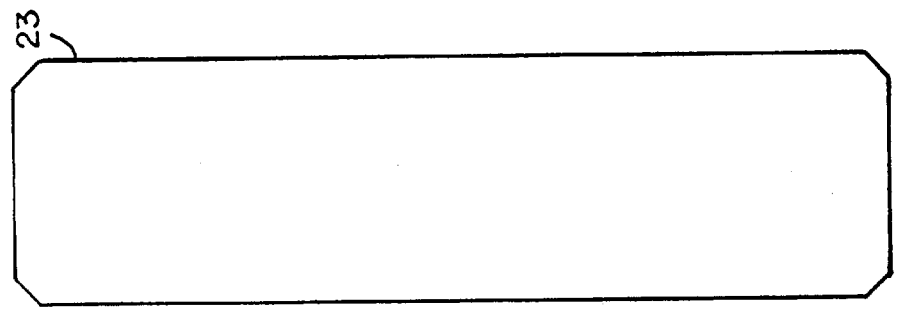
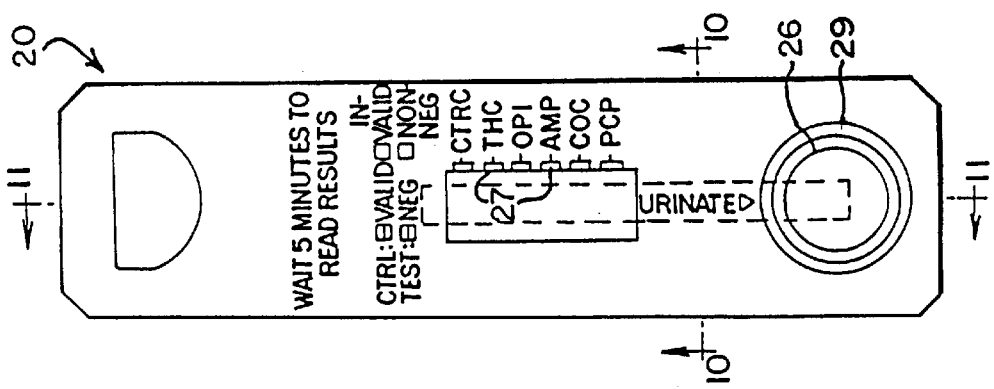

DISPOSABLE DEVICES FOR TESTING BODY FLUIDS

BACKGROUND AND DESCRIPTION OF THE INVENTION

This invention relates generally to self-contained disposable devices for use in testing body fluid specimens for the presence of one or more foreign substances or for the presence of a normally occurring substance in an abnormal concentration. In one embodiment of the invention the device is in the form of a liner for a closure cap to be applied to a container in which a body fluid specimen has been collected. Preferably, the testing device in the form of a cap liner provides a liquid-tight seal between the closure cap and the container so that when the container is inverted with a liquid body fluid specimen on the inside there will be no leakage. In another form of the invention the device is paddle-shaped so that it can be either dipped into a body fluid specimen collected in an open container or inserted into a stream of the specimen, with a test strip mounted in the device becoming wet with the fluid specimen.

Routinely, in doctors' offices, clinics, hospitals, places of employment, persons are required to introduce urine specimens into small open cups or containers for subsequent testing by technicians, nurses or other health-care personnel. Reagent strips or wicks are widely available and commonly used to test the urine specimens for the presence of various substances including glucose, bilirubin, ketone, blood, protein, urobilinogen, nitrite, and leukocytes as well as for specific gravity and pH. Such reagent strips usually consist of a wick or strip of material along the length of which color changing reagents are located in spaced relationship. As currently used, the person doing the testing wets the various test reagents with a urine specimen and then waits for color or appearance changes to take place and thereupon "reads" the reagent strip and notes the test results. In addition to testing body fluids such as urine for naturally occurring substances as in abnormal concentration, urine testing has become increasingly used to test for drugs and various controlled substances. For example, new job applicants are routinely tested for the presence of drugs in the urine and employees in critical jobs such as airline pilots, police, members of the defense establishment etc. are routinely screened for the presence of drugs or controlled substances in the urine.

Because of the increased frequency and wider need for testing urine and other body fluids such as blood, there is an increased demand and need for inexpensive testing devices that lend themselves to simplified testing procedures carried out by persons not highly trained or skilled, including laymen capable of following simple written instructions.

Accordingly, the object of the present invention, generally stated, is the provision of self-contained disposable devices for testing urine and other body fluids which are economical to produce, easy to use with good results and adaptable to a wide variety of testing requirements.

For a complete understanding of the nature and scope of the invention reference may be had to the following detailed description of preferred embodiments thereof taken in connection with the accompanying drawings wherein:

BRIEF DESCRIPTION OF THE DRAWINGS

FIG. 7 is a plan view of the results-of-the-test side of a urine testing device in the form of a paddle to be dipped into an open specimen or insertion in a stream of urine or other body fluid;

FIG. 8 is a view of the reverse or underside of the device shown in FIG. 7;

FIG. 9 is a plan view of the intermediate ply of the three ply composite forming the device of FIGS. 7 and 8;

FIG. 10 is a sectional view on enlarged scale taken on line 10—10 of FIG. 7; and FIG. 11 is a fragmentary sectional view on enlarged scale taken on line 11—11 of FIG. 7.

Figure 1:
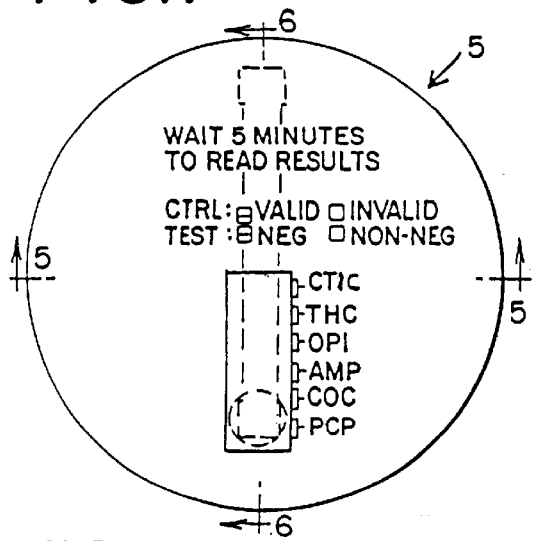
FIG. 1 is a plan view of the results-of-the-test side of a circular or disc shaped device for testing urine and being in the form of a composite of three plies laminated together with a test strip confined therein.

The embodiment of the invention shown and illustrated in FIGS. 1–6 takes the form of a composite disc which may be used as the liner of the transparent closure cap for a specimen container to provide a liquid-tight seal between the closure cap and the rim of the container or jar.

The device of FIGS. 1–6 is indicated generally therein at 5. While these dimensions are not critical the device 5 may have a thickness of $\frac{1}{16}$ of an inch (0.0625). The middle or intermediate ply 6 (FIGS. 3 and 4) of the 3-ply composite forming the device 5 accounts for most of its total thickness since the two outer plies are formed of thin transparent plastic sheet material. The relatively thick intermediate ply 6 is formed of a non-absorbent material such as closed cell polyethylene which is inert to, and not wetted by urine or other body fluids. The inner ply 6 is formed with an elongated opening 7 into which a test wick or strip 8 (FIG. 4) is inserted with a friction fit.

Figure 2:
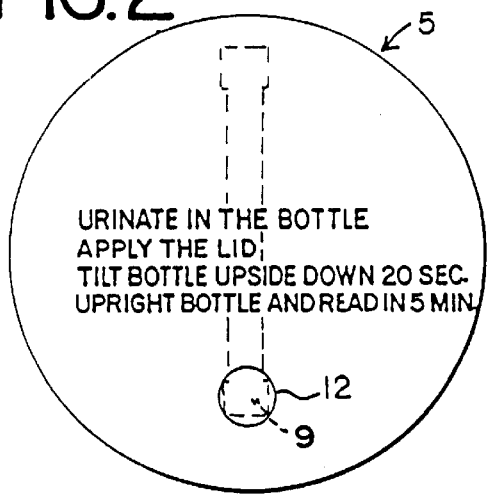
FIG. 2 is a view of the reverse or opposite side of the device shown in FIG. 1.
Figure 3:
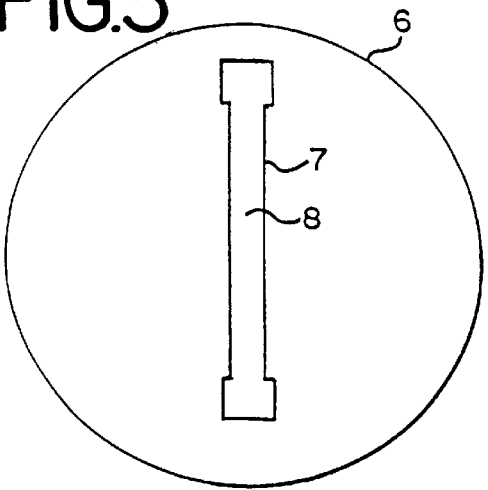
FIG. 3 is a plan view of the intermediate ply of the device shown in FIGS. 1 and 2.
Figure 4:
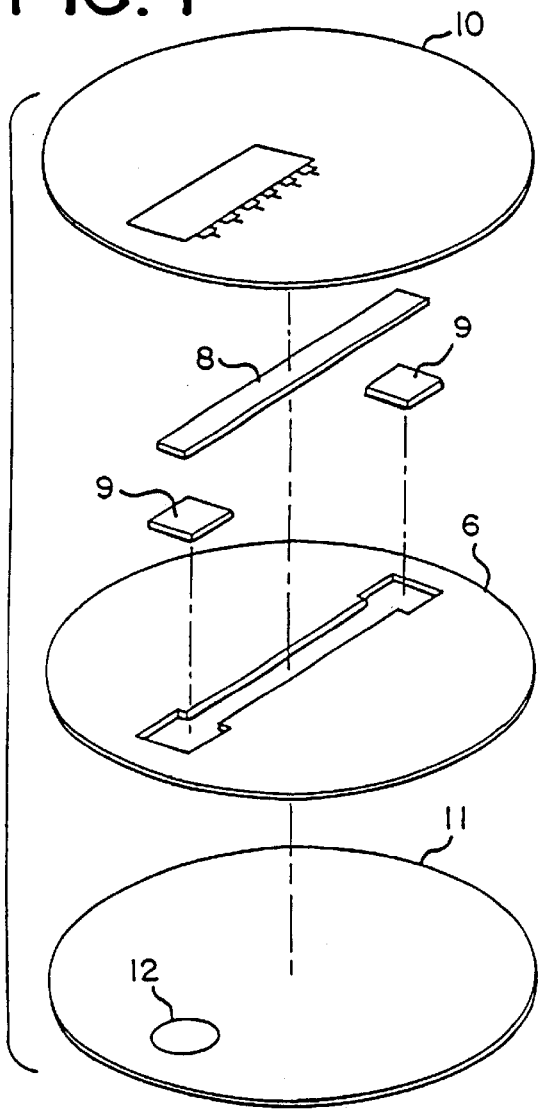
FIG. 4 is an exploded view of the device shown in FIGS. 1–3.
Figure 5:
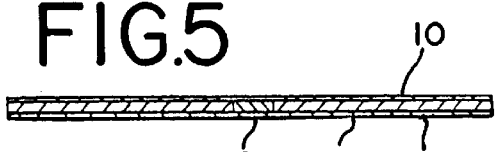
FIG. 5 is a sectional view taken on line 5—5 of FIG. 1.
Figure 6:
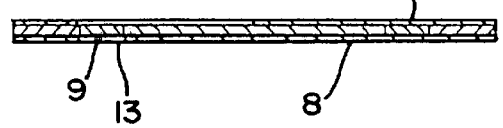
FIG. 6 is a sectional view taken on line 6—6 of FIG. 1.

The top ply 10 (FIG. 4) and bottom ply 11 may be formed, for example, of a transparent polyester sheet material which is non-absorbent. The top ply or disc 10 is clear, or transparent at least in the area lying over the elongated opening 7 (FIG. 1) containing the wick or test strip 8 and is provided with suitable printing in the form of lettering and geometric designs. In addition to the wording such as "Wait five minutes to read results" the top disc 10 has six blocks arranged along one side of the opening 7 and labeled in descending order: CTIC; THC; OPI; AMP; COC; and PCP. These designations are abbreviations for: control; marijuana; opiates; amphetamines; cocaine; and phenacylidine, respectively. Additional information and instructions can be applied on the opposite or underside of the device 5 as indicated in FIG. 2.

Either of the outer discs or plies 10 or 11 may be provided with a small opening 12 (FIGS. 2 and 4) which provides a passageway allowing urine or other body fluid specimens to have access to the test strip 8. Preferably the opening 12 is filled or covered with reticle or membrane 13 which acts as a one-way valve to allow liquids to flow in and wet the opposite or underlying absorbent pad 9 in engagement with the adjacent end of the wick 8 as shown in FIGS. 1, 2, 4 and 6. The reticle may be formed of cellulose acetate or urethane. As shown, the plies 6, 10 and 11 are substantially co-extensive.

If the device 5 is to be used as the liner in a transparent closure cap the device 5 should be inserted so that the results can be read through the top of the closure cap and the opening 12 should be in the bottom ply 11 so that it will provide access of the contents of the container to the test wick 8 when the specimen container (not shown) is inverted.

Usually closure caps of the type that go on wide mouth containers will have annular recesses in the side wall in which cap liners may be inserted with acceptable temporary distortion, and retained. Otherwise the devices 5 can be secured in place by small amounts of adhesive. Preferably, the disc shaped test devices 5 also provide the liquid type seal between the closure cap and the mouth of the container.

Those skilled in the art are knowledgeable with respect to the placement of the different testing reagents in spaced relationship on the test strip 8 with the result that the test strip acts as a wick and the urine or other liquid specimen flows through the length of the wick and rapidly exposes each of the test reagents to the specimen. A visual color change will take place at the locations of the test reagents that are contacted by a substance in the urine or specimen to which they are visually responsive.

From the foregoing the manner of use of the device 5 will be readily apparent. The user places a specimen of urine or other liquid in an open specimen container and then applies the closure cap with the testing device 5 already inserted therein with the proper orientation. The closure cap is tightened on the container sufficiently to produce a fluid-tight seal between disk 5 in the cap and the mouth of the container when the container is inverted so as to bring the specimen in contact with the wick 8 by way of the passage provided by the opening 12 and one-way valve 13. After an appropriate time of inversion (e.g. five minutes), the container is righted so that the results can be read through the closure cap.

A second embodiment of the invention in the form of a paddle or stirrer is indicated generally at 20 in FIGS. 7–11. This embodiment will be used in connection with urine or other liquid specimens usually collected in open containers. The paddle 20 may-comprise three plies laminated together and corresponding generally in construction to the disc-shaped testing device 5 of FIGS. 1–6. Referring particularly to FIGS. 10 and 11 the paddle device 20 comprises a relatively thick non-absorbent intermediate layer 21 which corresponds to the intermediate layer 6 in FIGS. 3 and 4. A top ply of clear plastic with printing is designated at 22 while a bottom or underside clear plastic layer or ply is indicated at 23.

The relatively thick intermediate ply 21 has an elongated opening 24 for receipt and retention therein of the testing strip or wick 25. As shown, the plies 21, 22 and 23 are substantially co-extensive.

In order for the urine or other liquid specimen to have access to the test strip or wick 25 the ply 22 is provided with a small opening 26 (FIG. 7) located at the lower end of the test strip 25 and preferably covered with a reticle 29.

As in the case of the test strip 8 in the embodiment of FIGS. 1–6 different testing reagents will be deposited in the test strip 25 corresponding to the six locations indicated at 27 in FIG. 7.

In use the user of the paddle device 20 will grasp it at its upper end and dip the lower end into the liquid specimen and move the lower end back and forth in the specimen so that the wick or test strip 25 becomes thoroughly wetted with the specimen. At that point the device 20 can be removed and either held or laid on a suitable support until adequate time has elapsed for the color changes to develop in the test strip 25 depending upon the substances present in the specimen. If desired the wick or test strip may become wetted by holding the opening 26 in a stream of urine.

It will be understood that if desired, the small opening 26 in the top ply 22 can be located in the ply 23', or there could be a small opening in both plies 22 and 23. It will be seen that in use the small openings 12 and 26 provide the only access of a body fluid specimen to the test wicks 8 and 25 respectively. Likewise, it will be understood that instructions or information can be printed on the ply 23.

While a laminate comprised of three or more plies provides a very satisfactory support or carrier for a test strip or wick, one or both outer plies can be omitted and the test strip or wick can be supported in a relatively thick ply of non-absorbent material, such as the closed cell polyethylene intermediate used for ply 6 in FIG. 2. For example, the wick 8 can be cemented in place and coated on one or both sides with a non-wettable coating except for a small wettable area at one end. A plastic strip printed with the various tests CTIC; THC etc. can be adhered to the support along side the wick.

As a further embodiment, one of the outer plies of the devices 5 and 20 may be omitted with the remaining outer ply covering the test wick and having a small opening 12, 26 for entry of test fluid.

What is claimed is:

1. A self-contained disposable device to be used in testing a body fluid specimen for the presence therein of one or more foreign substances or for the presence therein of a naturally occurring substance in an abnormal concentration, comprising, in combination, a multi-ply composite of substantially co-extensive plies and a wettable test wick secured therein, said composite comprising a non-absorbent intermediate ply in which said wettable test wick is located, second and third non-absorbent plies laminated to opposite sides of said intermediate ply and substantially co-extensive therewith, at least one of said second and third non-absorbent plies being transparent in at least the area thereof covering said test wick, at least one of said second and third plies having a small passageway therein providing communication for body fluid with said test wick, and said test wick containing at least one deposit of at least one test reagent which gives a visual response when contacted by a body fluid containing a substance to which said test reagent is visually responsive said small passageway providing the only access of the body fluid specimen to said wettable test wick.

2. The device called for in claim 1 in the form of a disc which may be used as a liner of a transparent closure cap to provide a fluid tight seal between the closure cap and a container on which said cap is applied and in which a body fluid specimen is collected.

3. The device called for in claim 1 in the form of a paddle to be inserted into a body or stream of a fluid specimen until said test wick becomes wetted by said specimen.

4. The device called for in claim 1 wherein said small passageway is filled or covered by a piece of plastic which allows fluid to flow through in essentially only one direction and into said intermediate ply.

5. The device called for in claim 1 wherein said intermediate layer is formed of closed cell polyethylene.

6. The device called for in claim 1 wherein an absorbent pad is located in said intermediate ply and in at least partial alignment with said small passageway so as to become wetted by said body fluid entering through said passageway and said test wick which is located in said intermediate ply having one end in wettable engagement with said absorbent pad.

7. The device called for in claim 6 wherein a second absorbent pad is located in said intermediate layer in engagement with the opposite end of said test wick.

8. The device called for in claim 1 wherein a plurality of segments of the wettable length of said test wick are impregnated with a corresponding plurality of test reagents.

9. The device called for in claim 8 wherein said test reagents include: a control and at least one selected from the group consisting of marijuana, opiates, amphetamines, cocaine, and phencyclidine.

* * * * *